United States Patent
Valente et al.

(10) Patent No.: US 9,062,744 B2
(45) Date of Patent: Jun. 23, 2015

(54) TWO-SPEED DRIVE MODULE

(71) Applicant: American Axle & Manufacturing, Inc., Detroit, MI (US)

(72) Inventors: Paul J. Valente, Berkley, MI (US); James P. Downs, South Lyon, MI (US)

(73) Assignee: American Axle & Manufacturing, Inc., Detroit, MI (US)

( * ) Notice: Subject to any disclaimer, the term of this patent is extended or adjusted under 35 U.S.C. 154(b) by 0 days.

(21) Appl. No.: 14/159,534

(22) Filed: Jan. 21, 2014

(65) Prior Publication Data

US 2014/0274528 A1    Sep. 18, 2014

Related U.S. Application Data

(60) Provisional application No. 61/779,780, filed on Mar. 13, 2013.

(51) Int. Cl.
| | | |
|---|---|---|
| *F16H 48/06* | (2006.01) | |
| *F16H 3/54* | (2006.01) | |
| *B60K 1/00* | (2006.01) | |

(52) U.S. Cl.
CPC ............ *F16H 3/54* (2013.01); *B60K 2001/001* (2013.01); *F16H 2200/0034* (2013.01); *F16H 2200/2005* (2013.01)

(58) Field of Classification Search
CPC .............. B60K 6/20; B60K 6/26; B60K 6/54; B60K 6/365; B60K 6/383; B60K 6/387; B60K 6/445; B60K 6/584; B60K 6/547

USPC ............... 475/5, 149, 150–151, 220–221; 180/65.21, 65.235, 65.26, 65.6, 65.7
See application file for complete search history.

(56) References Cited

U.S. PATENT DOCUMENTS

| | | | | | |
|---|---|---|---|---|---|
| 4,418,777 | A | * | 12/1983 | Stockton | 180/65.6 |
| 5,651,749 | A | * | 7/1997 | Wilson et al. | 475/221 |
| 6,692,394 | B2 | * | 2/2004 | Takenaka | 475/5 |
| 7,416,505 | B2 | | 8/2008 | Downs | |
| 7,497,286 | B2 | * | 3/2009 | Keller et al. | 180/65.6 |
| 8,403,088 | B2 | * | 3/2013 | Knoblauch et al. | 180/65.7 |
| 8,505,658 | B2 | * | 8/2013 | Wargh et al. | 180/65.51 |
| 2004/0055800 | A1 | * | 3/2004 | Katou et al. | 180/65.2 |
| 2008/0190729 | A1 | | 8/2008 | Stehr et al. | |
| 2010/0240485 | A1 | * | 9/2010 | Strasser et al. | 475/150 |
| 2011/0218070 | A1 | * | 9/2011 | Mack et al. | 475/150 |
| 2011/0237387 | A1 | | 9/2011 | Yang | |
| 2013/0203543 | A1 | | 8/2013 | Sten | |
| 2013/0303324 | A1 | | 11/2013 | Valente et al. | |
| 2013/0303326 | A1 | | 11/2013 | Downs et al. | |
| 2013/0337960 | A1 | | 12/2013 | Valente et al. | |

FOREIGN PATENT DOCUMENTS

WO   WO-2009/067416   5/2009

\* cited by examiner

*Primary Examiner* — Robert Hodge
*Assistant Examiner* — Tinh Dang
(74) *Attorney, Agent, or Firm* — Harness, Dickey & Pierce, P.L.C.

(57) ABSTRACT

A drive module that includes an electric motor and a multi-speed transmission assembly having a two-speed planetary transmission stage. The multi-speed transmission assembly outputs rotary power to a differential assembly.

22 Claims, 11 Drawing Sheets

TWO-SPEED DRIVE MODULE

CROSS-REFERENCE TO RELATED APPLICATIONS

This application claims the benefit of U.S. Provisional Patent Application No. 61/779,780 field Mar. 13, 2013, the disclosure of which is incorporated by reference as if fully set forth in detail herein.

FIELD

The present disclosure relates to a two-speed drive module.

BACKGROUND

This section provides background information related to the present disclosure which is not necessarily prior art.

It is known in the art to provide an all-wheel drive vehicle drive train that provides drive torque to the front and rear wheels of a vehicle on either a full-time basis or a part-time but automatically-engaging basis. The known full-time all-wheel drive configurations typically utilize a transfer case or power transfer unit and a center differential or coupling to distribute drive torque to a front differential, which in turn distributes drive torque to the set of front wheels, and a rear differential, which in turn distributes drive torque to the set of rear wheels. The known part-time all-wheel drive configurations typically utilize a power transmitting coupling that permits a set of wheels (e.g., the rear wheels) to coast until the other set of wheels (e.g., the front set of wheels) begin to loose traction.

One drawback of these all-wheel drive arrangements concerns their complexity and overall cost. Not only are the components of the all-wheel drive system relatively complex and costly to manufacture and install, the associated vehicle architecture is frequently more complex due to the common practice of vehicle manufacturers to offer vehicles with a standard two-wheel configuration and an optional all-wheel drive configuration. In this regard, it is frequently necessary to modify the vehicle fuel tank and/or relocate the spare tire of the vehicle to incorporate a conventional four-wheel drive system into a two-wheel drive vehicle.

One proposed solution involves the use of wheel hub motors. In these systems, relatively large electric motors are placed within the circumference of two or more of the vehicle wheels. As wheel hub motors are relatively large in diameter, the size of the wheel tends to be relatively large (i.e., 18 inches or greater). Consequently, wheel hub motors may not be practical as when a relatively small wheel size is employed or where packaging issues, such as the size and location of a fuel tank or the location of a spare tire, prevent a wheel hub motor from being integrated into the vehicle.

One relatively recent innovation in all-wheel drive vehicles is a drive module that employs an electric motor, a transmission and a differential to selectively drive a set of vehicle wheels. Such drive modules are gaining acceptance with automotive original equipment manufacturers in hybrid vehicles and may at some point be employed as the sole source of propulsive power in an electric vehicle. While the known drive modules are satisfactory for their intended purposes, there remains a need in the art for an improved drive module.

SUMMARY

This section provides a general summary of the disclosure, and is not a comprehensive disclosure of its full scope or all of its features.

In one form, the present teachings provide a drive module that includes an electric motor, a differential assembly, a multi-speed transmission assembly, and a pair of axle shafts, the differential assembly having a differential input member and a pair of differential output members. The multi-speed transmission assembly being configured to transmit rotary power between the electric motor and the differential input member. The multi-speed transmission assembly includes a housing, a two-speed planetary transmission stage, a first clutch, a second clutch and a transmission output member. The two-speed planetary transmission stage has a sun gear, a ring gear, a plurality of planet gears and a planet carrier. The sun gear is the input of the two-speed planetary stage. The planet gears are meshed with the sun gear and with the ring gear. The planet gears are rotatably mounted on the planet carrier. One of the planet carrier and the ring gear is the output of the two-speed planetary transmission stage and is drivingly coupled to the transmission output member. The first clutch is selectively operable for locking the two-speed planetary transmission stage such that it operates in a 1:1 gear ratio. The second clutch is operable for controlling rotation of the other one of the planet carrier and the ring gear. The transmission output member is meshingly engaged to the differential input member. Each of the axle shafts is coupled to an associated one of the differential output members for rotation therewith.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
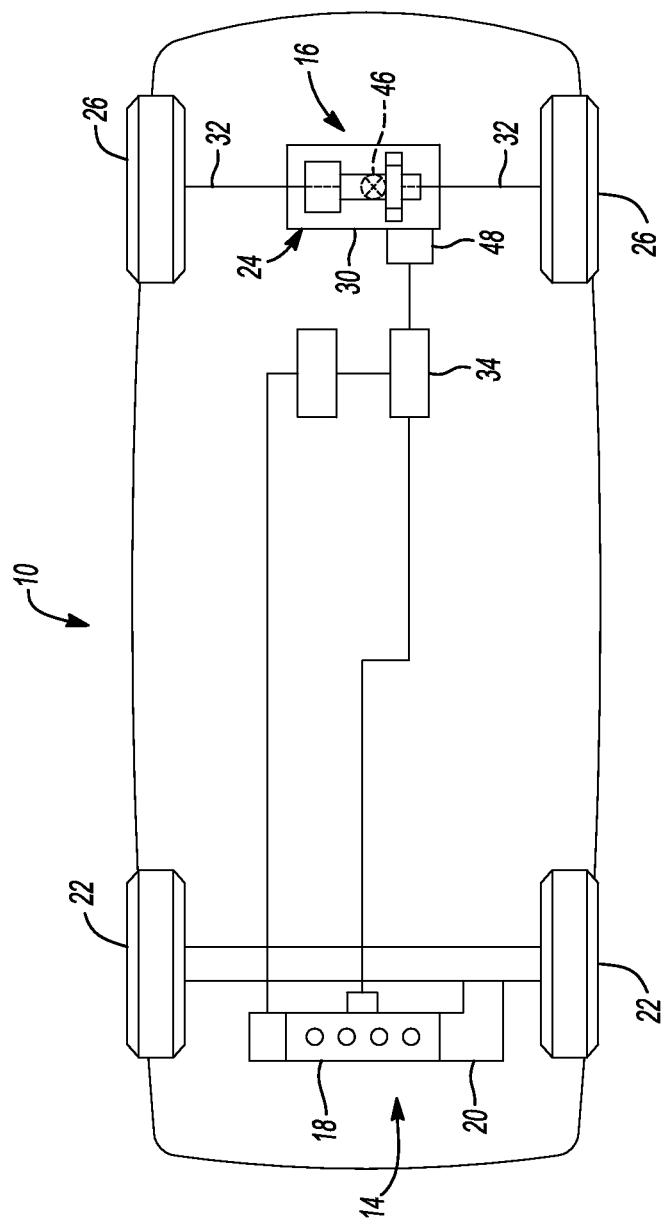
FIG. 1 is a schematic illustration of an exemplary vehicle having a drive module constructed in accordance with the teachings of the present disclosure.

With reference to FIG. 1 of the drawings, an exemplary vehicle having a drive module constructed in accordance with the teachings of the present disclosure is generally indicated by reference numeral 10. The vehicle 10 can include a front or primary driveline 14 and a rear or secondary driveline 16. The front driveline 14 can comprise an engine 18 and a transmission 20 and can be configured to drive a front or primary set of drive wheels 22. The rear driveline 16 can comprise a drive module 24 that can be configured to drive a rear or secondary set of drive wheels 26 on an as needed or "on demand" basis. While the front wheels 22 are associated with the primary driveline 14 and the rear wheels 26 are associated with the secondary driveline 16 in the present example, it will be appreciated that in the alternative, the rear wheels could be driven by the primary driveline and the front wheels could be driven by the secondary driveline. Moreover, while the drive module 24 has been depicted in this example as being configured to drive a secondary set of drive wheels on a part time basis, it will be appreciated that a drive module constructed in accordance with the present teachings could be employed to drive a (front, rear or other) set of drive wheels (e.g., a front or set of wheels) on a full-time basis, either as the sole means of propulsion for the vehicle or in conjunction with another means of propulsion. The drive module 24 can comprise a drive unit 30, a pair of axle shafts 32, and a controller 34.

Figure 2:
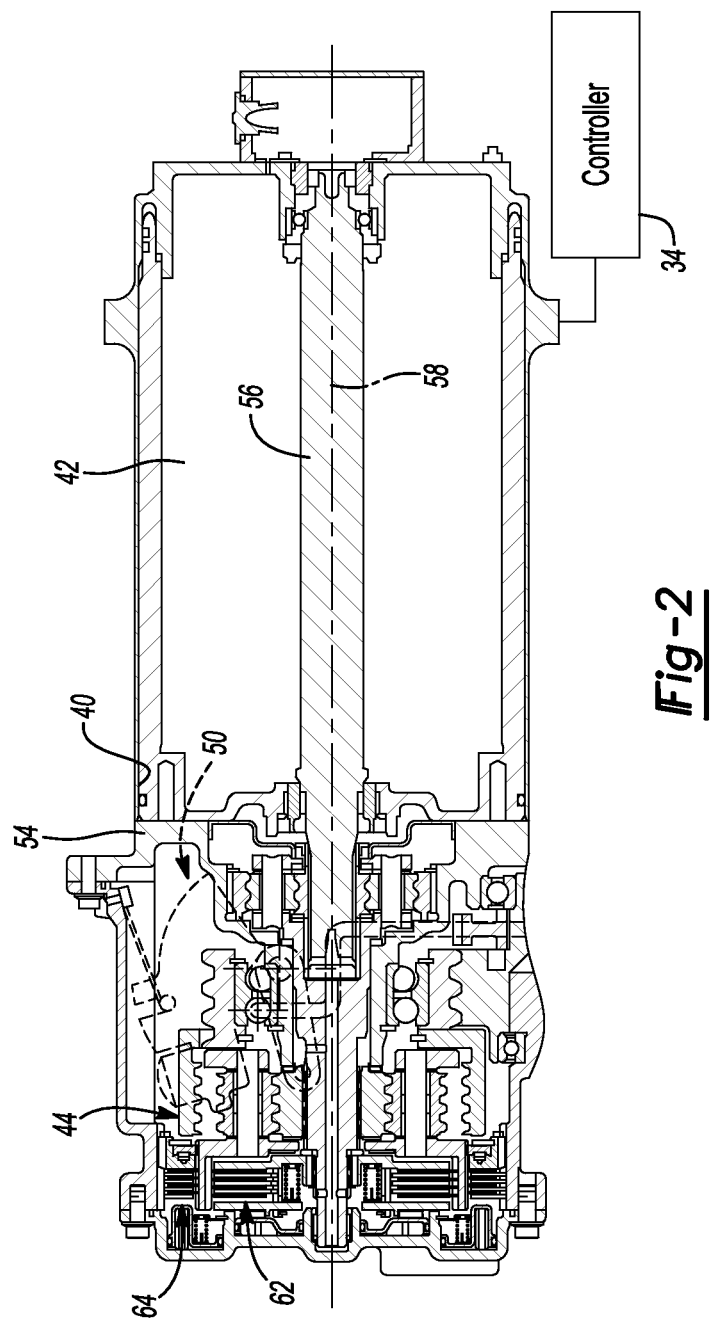
FIG. 2 is a section view of a portion of the vehicle of FIG. 1, illustrating a portion of the drive module that includes an electric motor and a multi-speed transmission assembly.

With reference to FIG. 2, the drive unit 30 can comprise a housing 40, an electric motor 42, a multi-speed transmission 44, a differential assembly 46 (FIG. 1), a hydraulic pump 48 (FIG. 1), and a park pawl mechanism 50.

The housing 40 can define a structure to which the other components of the drive unit 30 are mounted. The housing 40 can be formed of two or more housing elements that can be fixedly coupled together, such as via a plurality of threaded fasteners. The electric motor 42 can be mounted to a flange 54 on the housing 40 and can have an output shaft 56 that can be disposed along a first rotary axis 58 and received into the housing 40.

Figure 3:
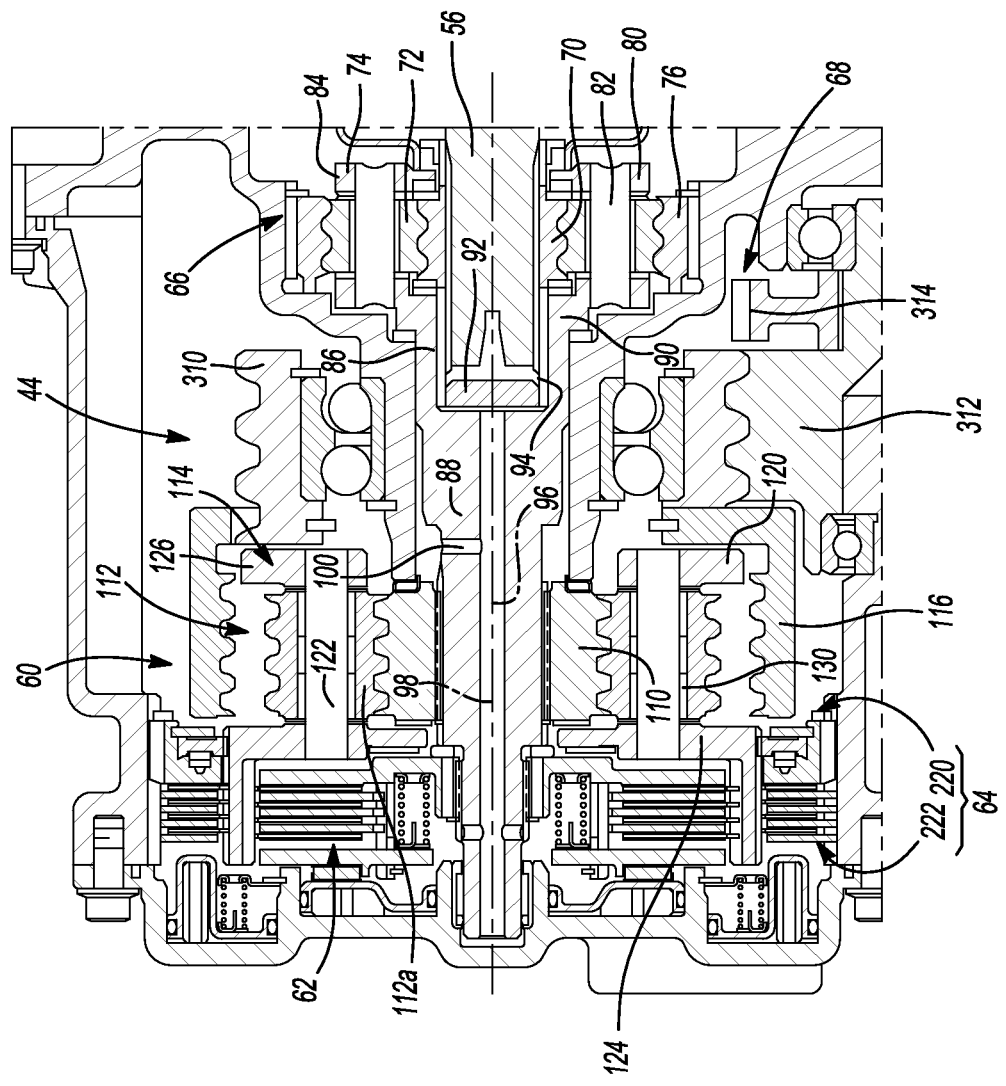
FIG. 3 is an enlarged view of the multi-speed transmission assembly.

In FIG. 3, the multi-speed transmission 44 can comprise a two-speed planetary transmission stage 60, a first clutch 62 and a second clutch 64. Optionally, the multi-speed transmission 44 can comprise one or more fixed reduction stages or gearsets, such as a first reduction gearset 66 and a second reduction gearset 68.

The first reduction gearset 66 can couple the motor output shaft 56 to the two-speed planetary transmission stage 60. In the example provided, the first reduction gearset 66 comprises a single planetary gearset, but it will be appreciated that any number and type(s) of gearsets could be employed. The first reduction gearset 66 can comprise a first sun gear 70, which can be coupled to the motor output shaft 56 for rotation therewith, a set of first planetary gears 72, a first planet carrier 74, and a first ring gear 76. The first planet gears 72 can be meshed to the first sun gear 70 and the first ring gear 76. The first planet carrier 74 can comprise a first carrier body 80 and a plurality of first pins 82. The first carrier body 80 can comprise a first body member 84, which can be a plate-like structure, and a second body member 86 that can comprise a shaft portion 88 and a flange 90. A shaft bore 92 can be formed into an end of the second body member 86 through the flange 90 and into the shaft portion 88. The shaft bore 92 can be sized to receive the output shaft 56. If desired, a bearing 94 can be received between the output shaft 56 and the inside surface of the shaft portion 88. One or more lubrication passages 96 can also be formed in the shaft portion 88. In the example provided, a main lubrication passage 98 is formed longitudinally through the shaft portion 88, and a plurality of feeder passages 100 intersect the main lubrication passage 98 and extend radially outwardly therefrom.

The two-speed planetary transmission stage 60 can include a second sun gear 110, a plurality of second planet gears 112, a second planet carrier 114, and a second ring gear 116. The second sun gear 110 can be coupled to the shaft portion 88 of the second body member 86 of the first planet carrier 74 for rotation therewith. Accordingly, it will be appreciated that the first planet carrier 74 can be an output member of the input planetary stage (i.e., the first reduction gearset 66), and that the second sun gear 110 can be an input member of an intermediate (or output) reduction gear set. The second planet carrier 114 can comprise a plurality of second pins 122 and a second carrier body 120 that can have first and second annular plates 124 and 126, respectively, that can be fixedly mounted to opposite ends of the second pins 122. The second planet gears 112 can be configured to transmit rotary power between the second sun gear 110 and the second ring gear 116. In the particular example provided, the second planet gears 112 comprise a set of inner planetary gears 112a and a set of outer planetary gears (not specifically shown). Each of the inner planetary gears 112a and each of the outer planetary gears can be mounted on the second pins 122 and if desired, a bearing 130 can be received between each of the second pins 122 and an associated one of the inner or outer planetary gears. Each of the inner planetary gears 112a can be meshingly engaged to the second sun gear 110, while each of the outer planetary gears can be meshing engaged to a corresponding one of the inner planetary gears 112a and the ring gear 116. While the two-speed planetary transmission stage 60 has been illustrated and described as having second planet gears 112 comprising inner and outer planetary gears, it will be appreciated that in the alternative, the second planet gears 112 could be configured such that each of the second planet gears 112 is meshingly engaged with both the second sun gear 110 and the second ring gear 116. The second ring gear 116 can be an output member of the multi-speed transmission 44.

Figure 4:
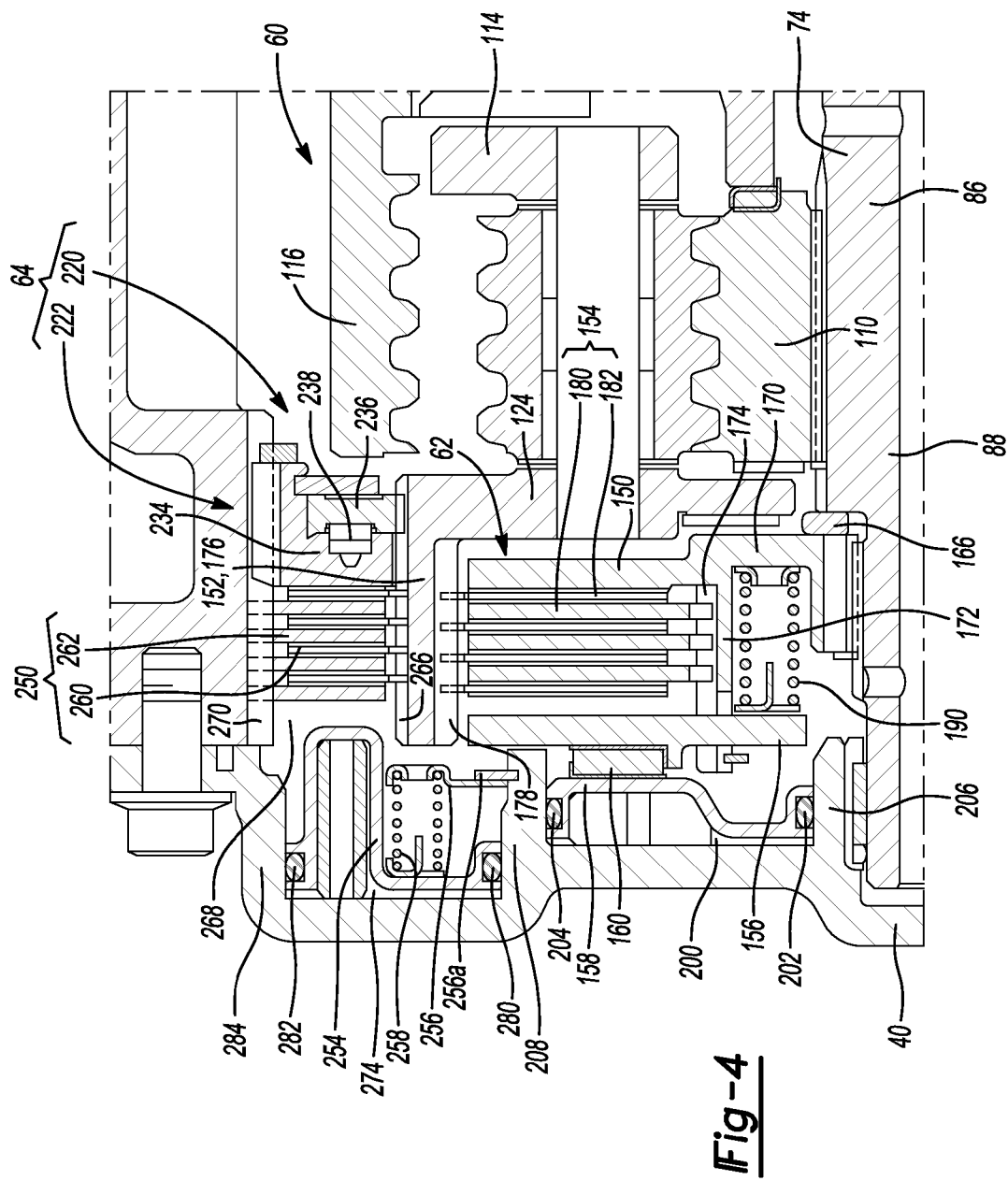
FIG. 4 is an enlarged portion of FIG. 3.

In FIG. 4, the first clutch 62 can be any type of clutch that can selectively couple the second ring gear 116 to the second sun gear 110 to lock the two-speed planetary transmission stage 60 (i.e., so that the two-speed planetary transmission stage 60 operates at a gear ratio of about 1:1). In the particular example provided, the first clutch 62 comprises a friction clutch having an input member 150, an output member 152, a set of clutch plates 154, a pressure plate 156, a piston 158 and a thrust bearing 160.

The input member 150 can be coupled to the shaft portion 88 of the second body member 86 of the first planet carrier 74 for rotation therewith. In the example provided, the input member 150 and the shaft portion 88 are rotatably coupled to one another via a set of mating splines or teeth, and a thrust washer 166, which is disposed between the input member 150 and a shoulder on the shaft portion 88, is employed to limit axial movement of the input member 150 in a direction away from the piston 158. The input member 150 can have a radially extending flange member 170 and an annular first clutch drum 172 that can extend axially outwardly from the flange member 170. The first clutch drum 172 can have a plurality of teeth 174 about its circumference. The teeth 174 extend axially and are circumferentially spaced about the exterior perimeter of the first clutch drum 172. The output member 152 can comprise an annular second clutch drum 176 that can be fixedly coupled to the first annular plate 124 of the second planet carrier 114. The second clutch drum 176 can have a plurality of circumferentially spaced apart internal teeth 178 that can extend in an axial direction. The set of clutch plates 154 can comprise a plurality of first clutch plates 180 and a plurality of second clutch plates 182. The first clutch plates 180 can comprise a suitable friction material and can have a toothed internal aperture that is sized to fit over the first clutch drum 172 and drivingly engage the teeth 174. The second clutch plates 182 can comprise a suitable friction material and can have an annular shape that is sized to be received into the second clutch drum 176. An outer perimeter of the second clutch plates 182 can be sized to be received in the second clutch drum 176 and to drivingly engage the teeth 178. The first and second clutch plates 180 and 182 can be interleaved. The pressure plate 156 can be an annular structure that can be non-rotatably but axially slidably received onto the first clutch drum 172 and abutted against the set of clutch plates 154. One or more compression springs 190 can be received in the first clutch drum 172 and abutted against the flange member 170 and the pressure plate 156. The compression spring(s) 190 can be configured to urge the pressure plate 156 axially away from the set of clutch plates 154 so that the first clutch 62 is normally disposed in a condition where rotary power is not transmitted between the input member 150 and the output member 152. The piston 158 can be an annular structure that can be received in an annular cavity 200 in the housing 40. The annular cavity 200 can be coupled in fluid connection to a source of hydraulic fluid. The piston 158 can carry seals 202 and 204 that can sealingly engage inner and intermediate annular walls 206 and 208, respectively, in the housing 40. The thrust bearing 160 can be disposed between the piston 158 and the pressure plate 156.

The second clutch 64 can be configured to selectively non-rotatably couple the second planet carrier 114 to housing 40. In the particular example provided, the second clutch 64 comprises a one-way clutch 220 and a second friction clutch 222. The one-way clutch 220 can be a type of self-activating clutch that permits rotation in a first rotational direction and inhibits rotation in an opposite rotational direction. In the particular example provided, the one-way clutch 220 is a sprag clutch having a first race 234, which is non-rotatably coupled to the housing 40, a second race 236, which is non-rotatably coupled to the second planet carrier 114, and a plurality of sprag rollers 238 that can interact with the first and second races 234 and 236 in a well-known and conventional manner to permit rotation of the second race 236 relative to the first race 236 in the first rotational direction and to inhibit rotation of the second race 236 relative to the first race 234 in the opposite rotational direction.

The second friction clutch 222 can comprise a set of clutch plates 250, a piston 254, a spring abutment 256, and one or more compression springs 258. The set of clutch plates 250 can comprise a plurality of third clutch plates 260 and a plurality of fourth clutch plates 262. The third clutch plates 260 can comprise a suitable friction material and can have a toothed internal aperture that is sized to fit over the second clutch drum 176 and drivingly engage axially extending teeth 266 that are disposed circumferentially about the exterior perimeter of the second clutch drum 176. The fourth clutch plates 262 can comprise a suitable friction material and can have an annular shape that is sized to be received over the second clutch drum 176. An outer perimeter of the fourth clutch plates 262 can be sized to be received in a cavity 268 in the housing 40 and to drivingly engage axially-extending teeth 270 that are spaced circumferentially about the cavity 268. The third and fourth clutch plates 260 and 262 can be interleaved.

The piston 254 can be an annular structure that can be received in an annular cavity 274 in the housing 40. The annular cavity 274 can be coupled in fluid connection to a source of hydraulic fluid. The piston 254 can carry seals 280 and 282 that can sealingly engage the intermediate annular wall 208 and an outer annular wall 284, respectively, in the housing 40. The spring abutment 256 can be an annular plate-like structure that can be received on the intermediate annular wall 208. An external snap ring 256a can be coupled to the intermediate annular wall 208 to inhibit axial movement of the spring abutment 256 in a direction toward the piston 254. The compression spring(s) 258 can be received axially between the piston 254 and the spring abutment 256 and can bias the piston 254 in a direction away from the set of clutch plates 250 so that the second friction clutch 222 is normally disposed in a condition where the second clutch drum 176 is not rotationally locked to the housing 40.

While the second clutch 64 has been described as including a one-way clutch 220 and a second friction clutch 222, it will be appreciated that the second clutch could be configured somewhat differently. For example, the one-way clutch 220 could be omitted altogether. Configuration in this manner would merely necessitate coordinated control of the first clutch 62 and the second friction clutch 222 as the two-speed planetary transmission stage 60 is shifted between speed reduction ratios (in contrast to the configuration that is described above and illustrated in the accompanying drawings, where coordinated control is unnecessary due to the self-activating nature of the one-way clutch 220).

As another example, a second actuator, such as a ball-ramp actuator (not shown), could be substituted for the one-way clutch 220. In this alternative construction, the ball-ramp actuator would tend to expand axially in response to rotation of the second planet carrier 114 in the first rotational direction and exerts an axially-directed force onto second friction clutch 222 that tends to compress the set of clutch plates 250 against the piston 254. Rotation of the second planet carrier 114 in the second rotational direction, however, tends to collapse the ball-ramp actuator in the axial direction so that the set of clutch plates 250 do not tend to inhibit rotation of the second planet carrier 114. Accordingly, the ball-ramp actuator can be employed to automatically inhibit rotation of the second planet carrier 114 when the two-speed planetary transmission stage 60 is operated in the low-speed reduction and the electric motor 42 is operated in the predetermined rotational direction, the ball-ramp actuator can be employed to automatically permit rotation of the second planet carrier 114 when the two-speed planetary transmission stage 60 is operated in the high-speed reduction and the electric motor 42 is operated in the predetermined rotational direction, and that the piston 254 of the second friction clutch 222 can be used to control lock-up of the set of clutch plates 250 to inhibit rotation of the second planet carrier 114 in the second rotational direction when the electric motor 42 is operated in a rotational direction that is opposite to the predetermined rotational direction.

As noted above, the second ring gear 116 is an output member of the multi-speed transmission 44. As such, the second ring gear 116 can be employed to directly drive the differential assembly 46 (FIG. 1). For example, the second ring gear 116 can be formed on or coupled to a differential case (not specifically shown) of the differential assembly 46 (FIG. 1) for common rotation.

Figure 5:
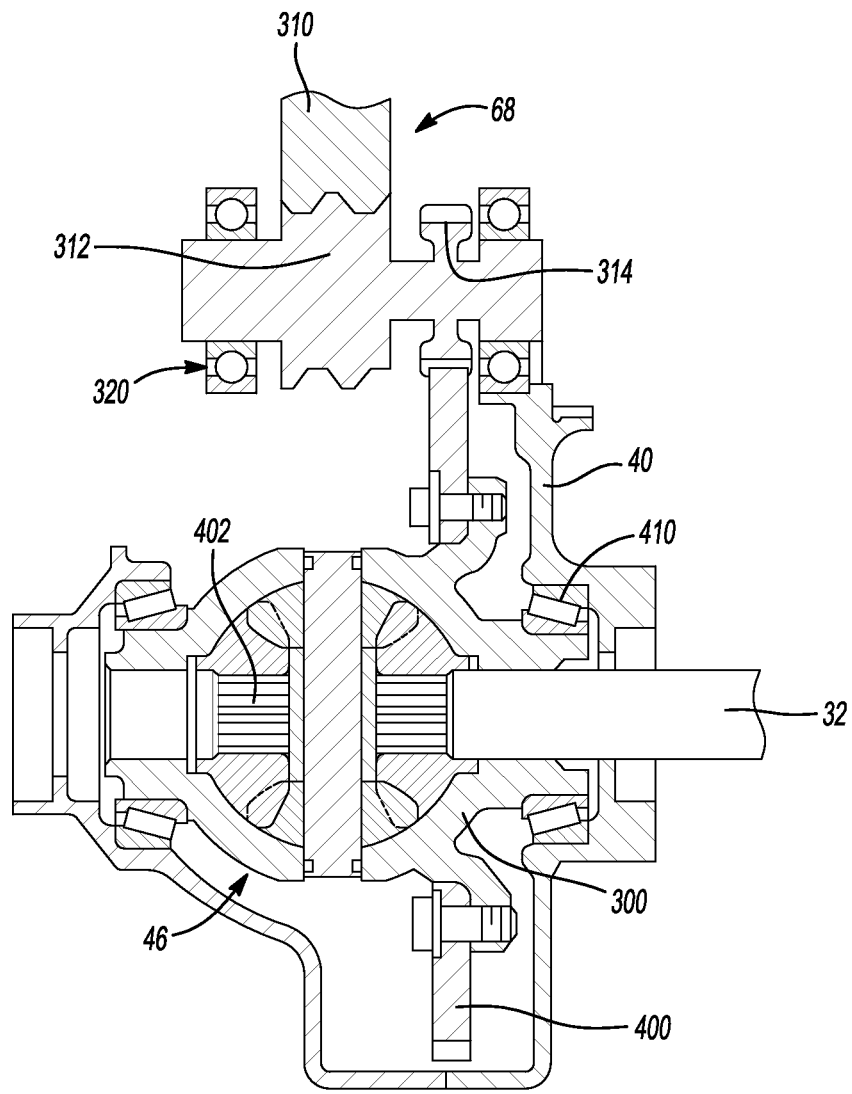
FIG. 5 is a section view of another portion of the vehicle of FIG. 1, illustrating a portion of the drive module that includes a differential assembly.

With reference to FIGS. 3 and 5, the second reduction gearset 68 can be configured in the alternative to transmit rotary power from the second ring gear 116 to a differential case 300 of the differential assembly 46. The second reduction gearset 68 can comprise a fixed reduction (as in the particular example provided) or a multi-speed reduction, and/or could include a mechanism that cooperates with the differential assembly 46 to provide torque vectoring capabilities in which equal but opposite vectoring moments are superimposed onto the outputs of the differential assembly 46.

In the particular example provided, however, the second reduction gearset 68 is a fixed reduction and can comprise a first helical gear 310, a second helical gear 312 and an output spur gear 314. The first helical gear 310 can be coupled to the second ring gear 116 for rotation therewith. As such, the first helical gear 310 is the input member of the second reduction gearset 68 in the example provided. The second helical gear 312 can be meshingly engaged with the first helical gear 310 and can be supported for rotation relative to the housing 40 via a pair of spindle bearings 320. The output spur gear 314 can be coupled to the second helical gear 312 for rotation therewith.

The differential assembly 46 can comprise an input ring gear 400, the differential case 300, a pair of output members 402, and a means for transmitting rotary power from the differential case 300 to the output members 402. The input ring gear 400 can be a spur gear that can be mounted to the differential case 300 and meshingly engaged to the output spur gear 314. The differential case 300 can be rotatably mounted to the housing 40 via a pair of differential bearings 410. The output members 402 can be received in the differential case 300 and can be non-rotatably coupled to an associated one of the axle shafts 32 (for clarity, only one axle shaft 32 is shown in FIG. 5).

Figure 6:
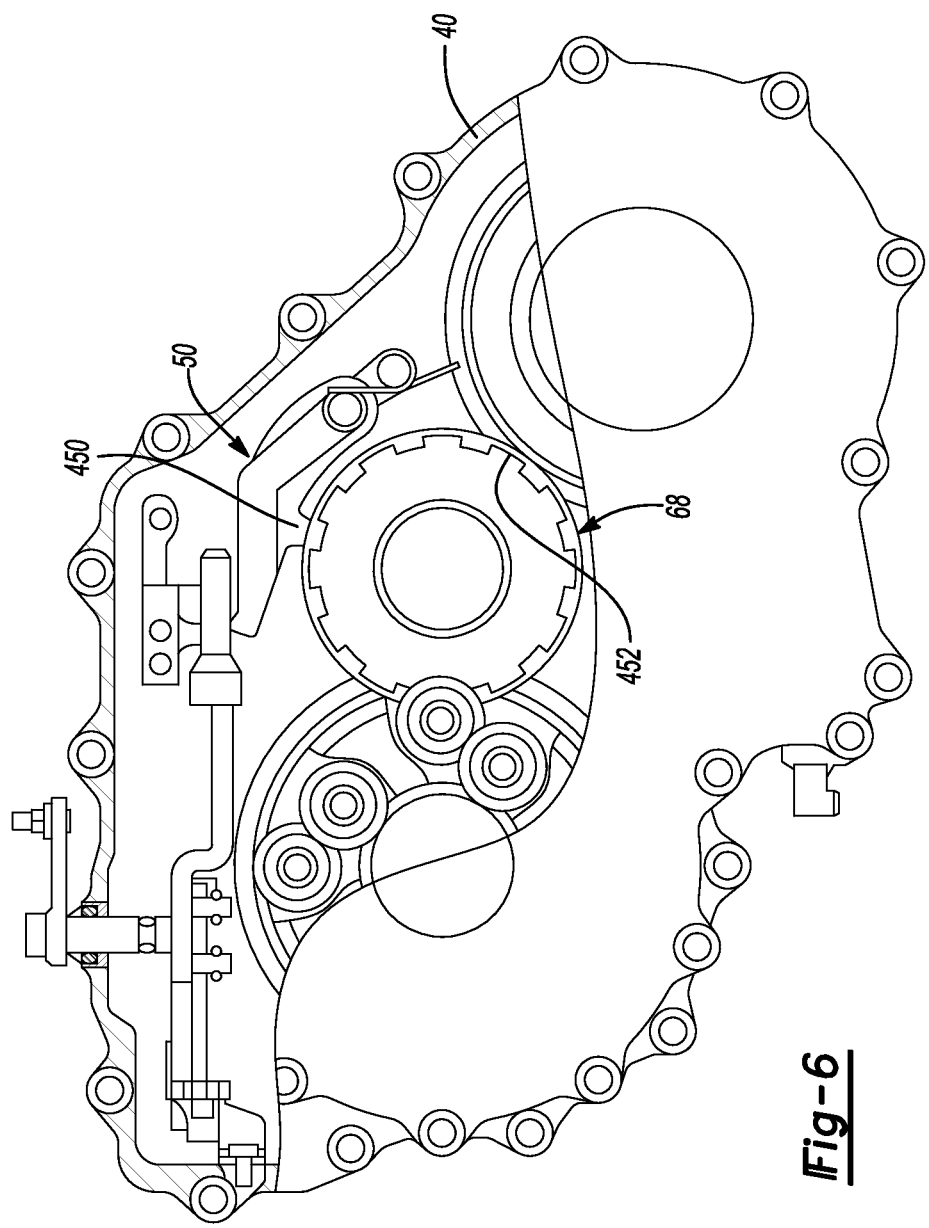
FIG. 6 is a left side elevation view of a portion of the vehicle of FIG. 1 illustrating the drive module in more detail.

In FIG. 6, the park pawl mechanism 50 can include a pawl member 450, which can be pivotally coupled to the housing 40, and a ratchet 452 that can be coupled to a member of the second reduction gearset 68 for rotation therewith. The pawl member 450 can be pivoted between a first or park position, in which the pawl member 450 is engaged between teeth of the ratchet 452, and a second position in which the pawl member 450 does not contact the teeth of the ratchet 452. It will be appreciated that when the pawl member 450 is in the first position, contact between the pawl member 450 and the teeth of the ratchet 452 will inhibit the transmission of rotary power through the second reduction gearset 68.

Figure 7:
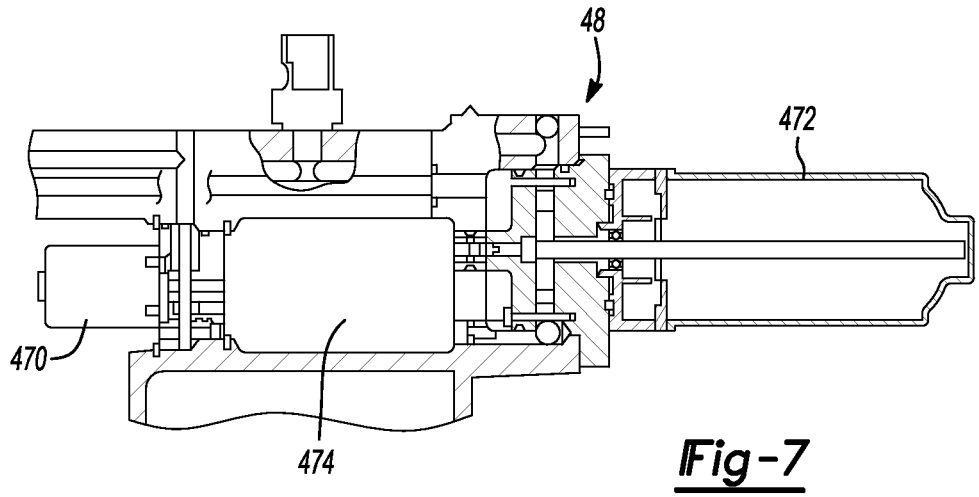
FIG. 7 is a section view of a portion of the drive module, illustrating a hydraulic pump in more detail.

With reference to FIG. 7, the hydraulic pump 48 can be configured to provide lubrication and/or fluid pressure for the activation of the first clutch 62 (FIG. 4) and/or the second clutch 64 (FIG. 4). In the particular example provided, the hydraulic pump 48 comprises a lubrication pump 470, which is configured to provide lubrication to various components within the drive module 24 (FIG. 1), and a servo-hydraulic unit 472 that is configured to coordinate the operation of the first clutch 62 and the second friction clutch 222. The lubrication pump 470 and the servo-hydraulic unit 472 could be configured in a separate manner so as to circulate different fluids. In the particular example provided, the lubrication pump 470 and the servo-hydraulic unit 472 are configured to draw fluid from a common reservoir 474.

Returning to FIG. 2, the controller 34 can be configured to control operation of the electric motor 42 and to coordinate operation of the first and second clutches 62 and 64. For example, the controller 34 can be configured to monitor or determine a speed of the vehicle 10 (FIG. 1), and/or a rotational speed of a component of the vehicle 10 (FIG. 1), such as a rotational speed of a component of the drive module 24 (FIG. 1), and to responsively control the operation of the first clutch 62 to control the gear ratio in which the multi-speed transmission 44 operates (i.e., to selectively lock the second planet carrier 114 to the second sun gear 110 for common rotation). As another example, the controller 34 can be configured to monitor a gear ratio setting of the transmission 20 (FIG. 1) and to responsively control the operation of the second friction clutch 222 if the transmission 20 (FIG. 1) has been placed into a reverse gear ratio.

Figure 8:
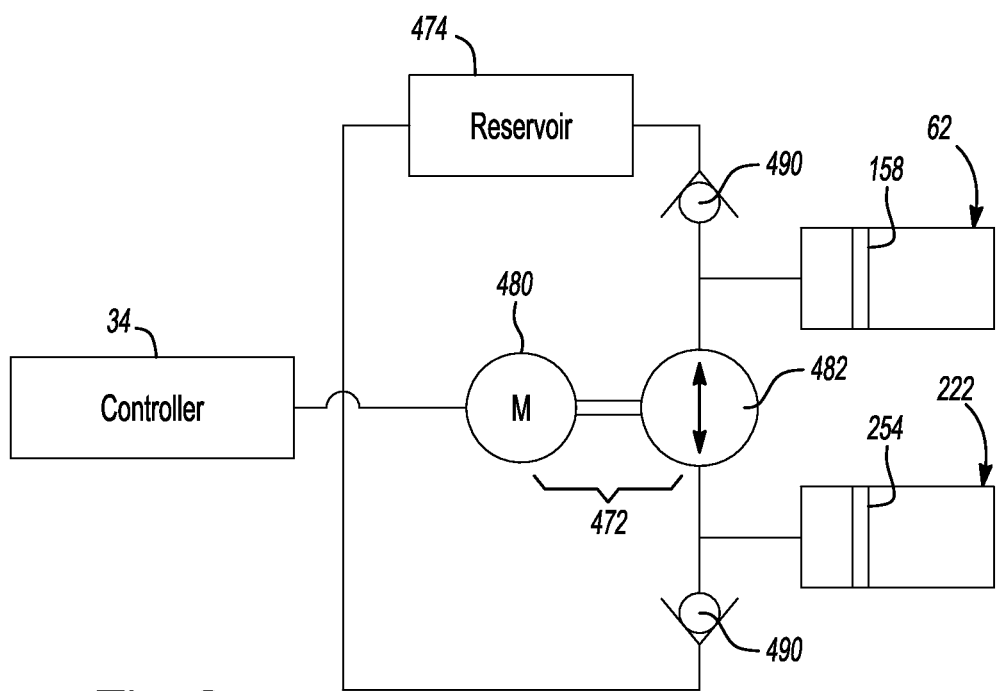
FIG. 8 is a schematic illustration of a portion of the drive module, illustrating a hydraulic circuit.

With reference to FIG. 8, the controller 34 can interact with the servo-hydraulic unit 472 to control the first clutch 62 and the second friction clutch 222. In the exemplary hydraulic circuit shown, the controller 34 is configured to control a rotary direction in which a reversible motor 480 of the servo-hydraulic unit 472 drives a reversible pump 482 that has a first inlet/outlet and a second inlet/outlet. Operation of the motor 480 in a first direction tends to apply hydraulic pressure to the piston 158 of the first clutch 62 and to draw hydraulic fluid from the second friction clutch 222. More specifically, operation of the motor 480 in a first rotational direction operates the pump 482 in the first rotational direction, so that the pump 482 draws hydraulic fluid into the first inlet/outlet from the reservoir 474 and an inlet/outlet of a hydraulic cylinder associated with the second friction clutch 222 through a first fluid conduit and transmits relatively higher pressure fluid out of the second inlet/outlet through a second fluid conduit to an inlet/outlet of a hydraulic cylinder associated with the first clutch 62. Operation of the motor 480 in a second, opposite direction tends to apply hydraulic pressure to the piston 254 of the second friction clutch 222 and to draw hydraulic fluid from the first clutch 62. More specifically, operation of the motor 480 in the second rotational direction operates the pump 482 in the second rotational direction so that the pump 482 draws hydraulic fluid into the second inlet/outlet from the reservoir 474 and the inlet/outlet of the hydraulic cylinder associated with the first clutch 62 through the second fluid conduit and transmits relatively higher pressure fluid out of the first inlet/outlet through the first fluid conduit to the inlet/outlet of the hydraulic cylinder associated with the second friction clutch 222. Check valves or other one-way valves 490 are employed in the hydraulic circuit to coordinate operation of the first clutch 62 and the second friction clutch 222 in the desired manner while still permitting the pump 482 to draw hydraulic fluid from the reservoir 474 when needed. In the example provided, a first one-way valve 490 is disposed in the first fluid conduit between the inlet/outlet port of the hydraulic cylinder associated with the second friction clutch 222 and the reservoir 474 and a second one-way valve 490 is disposed in the second fluid conduit between the inlet/outlet port of the hydraulic cylinder associated with the first clutch 62 and the reservoir 474.

Second Example

Figure 9:
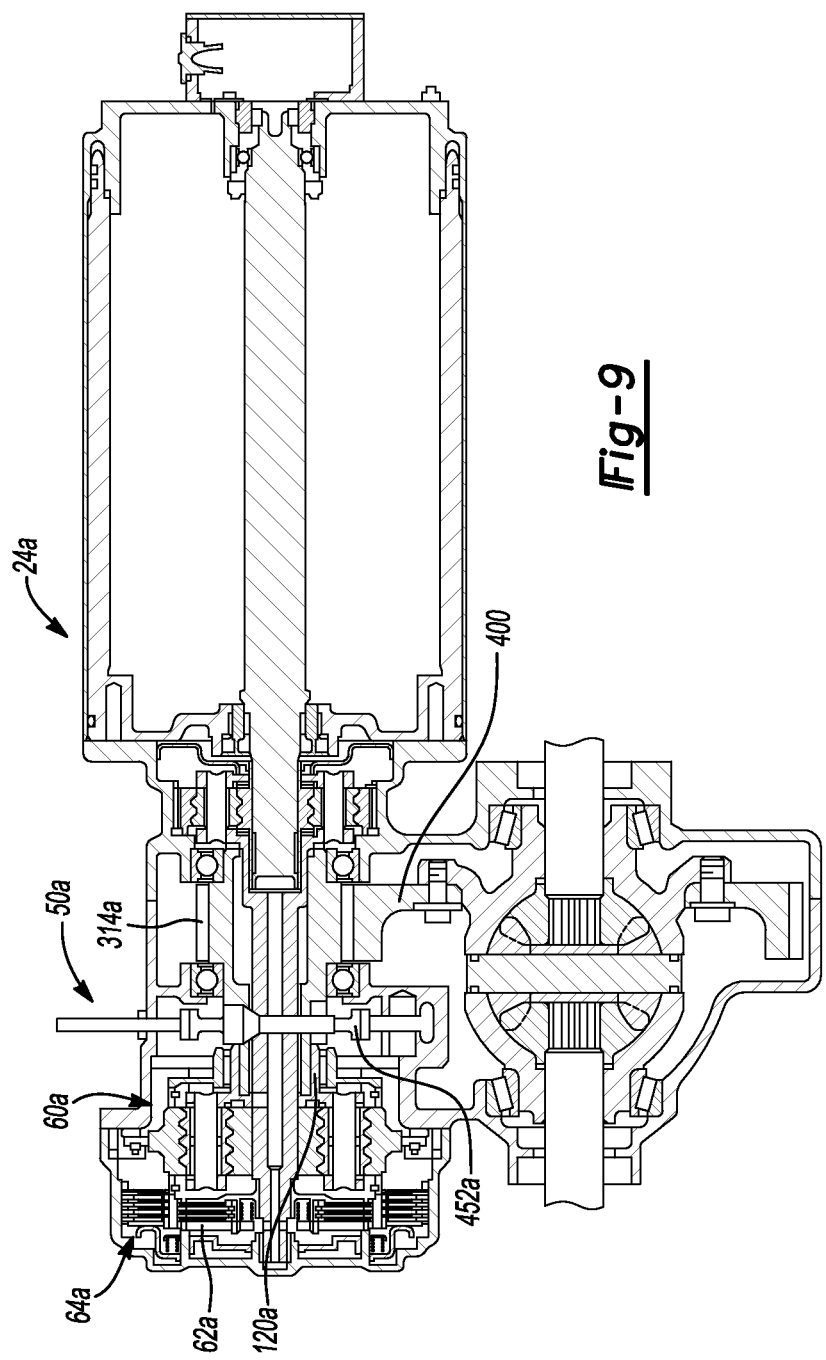
FIG. 9 is a section view of a portion of another drive module constructed in accordance with the teachings of the present disclosure.

In FIG. 9, a portion of a second drive module 24a constructed in accordance with the teachings of the present disclosure is illustrated. The drive module 24a can be generally similar to the drive module 24 (FIG. 1), except for the construction of the two-speed planetary transmission stage 60a, the first clutch 62a, the second clutch 64a, and the park pawl mechanism 50a.

Figure 10:
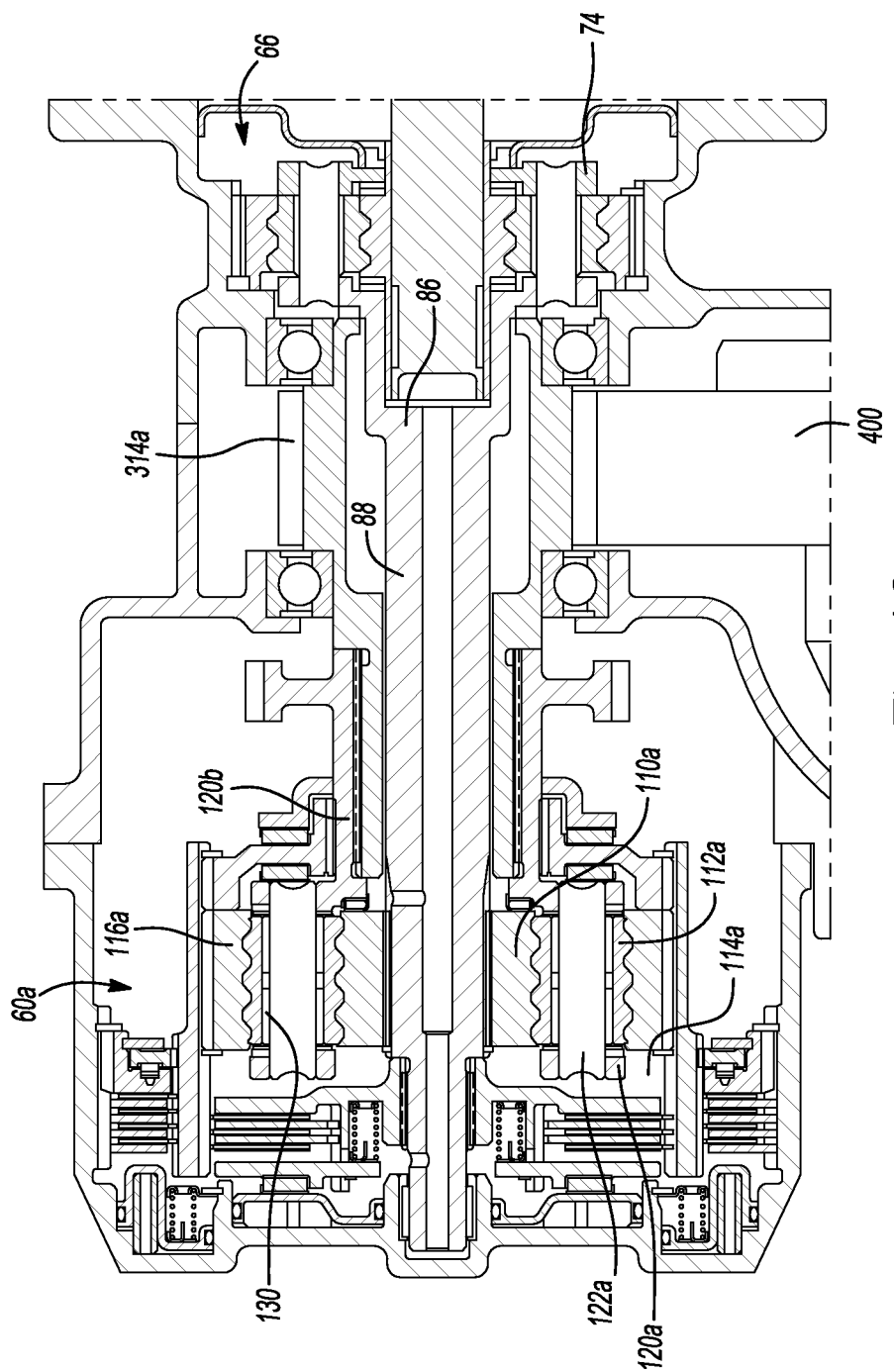
FIG. 10 is an enlarged portion of FIG. 9.

With reference to FIG. 10, the two-speed planetary transmission stage 60a can include a second sun gear 110a, a second planet carrier 114a, a plurality of second planet gears 112a, and a second ring gear 116a. The second sun gear 110a can be coupled to the shaft portion 88 of the second body member 86 of the first planet carrier 74 for rotation therewith. Accordingly, it will be appreciated that the first planet carrier 74 can be an output member of the input planetary stage (i.e., the first reduction gearset 66), and that the second sun gear 110a can be an input member of an intermediate (or output) reduction gear set. The second planet carrier 114a can comprise a plurality of second pins 122a and a second carrier body 120a that can have first and second annular plates that can be fixedly mounted to opposite ends of the second pins 122a. Each of the second planet gears 112a can be mounted on an associated one of the second pins 122a and can be meshingly engaged with the second sun gear 110a and the second ring gear 116a. If desired, a bearing 130 can be received between each of the second pins 122a and each of the second planet gears 112a. The second planet carrier 114a, and more specifically, the second carrier body 120a, can be an output member of the two-speed planetary transmission stage 60a. The carrier body 120a of the second planet carrier 114a can directly drive the first spur gear 314a.

Figure 11:
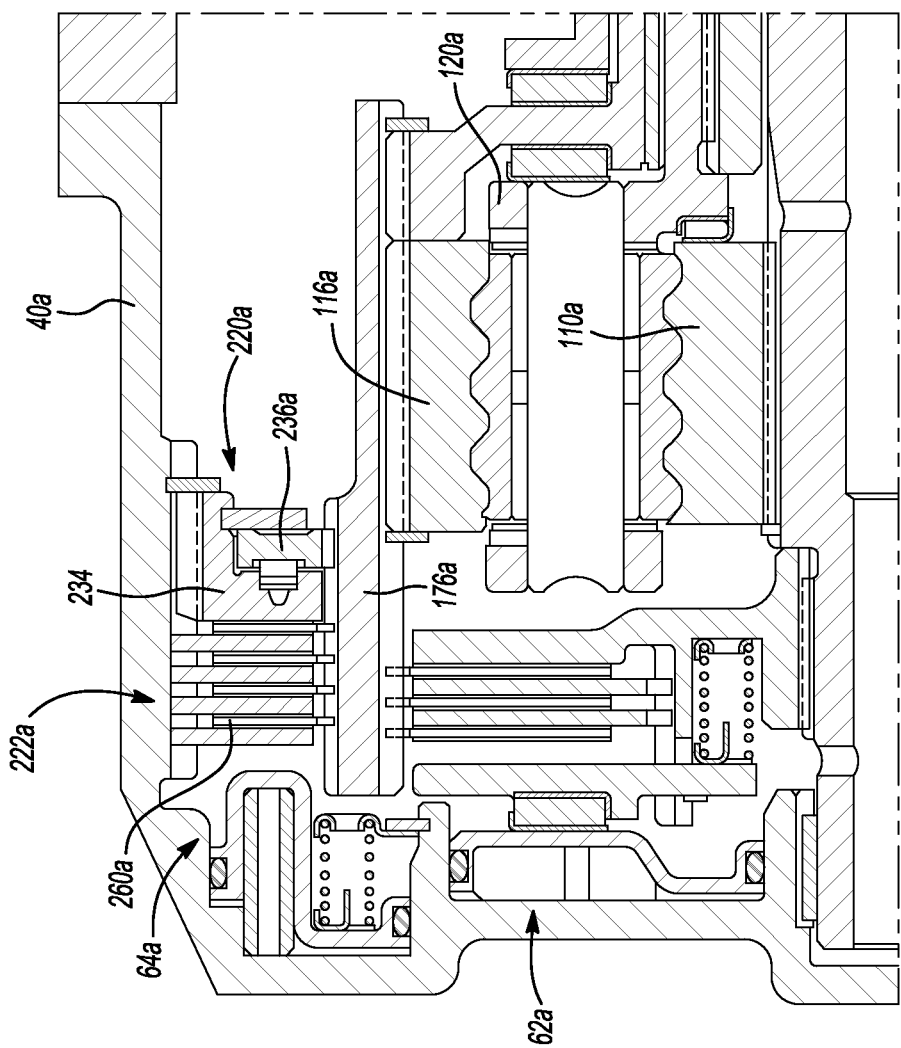
FIG. 11 is an enlarged portion of FIG. 10.

With reference to FIG. 11, the first clutch 62a can be any type of clutch that can selectively couple the second ring gear 116a to the second sun gear 110a to lock the two-speed planetary transmission stage 60a (i.e., so that the two-speed planetary transmission stage 60a operates at a gear ratio of about 1:1). In the particular example provided, the first clutch 62a is generally similar to the first clutch 62 (FIG. 4) except that the second clutch drum 176a is coupled to the second ring gear 116a (rather than to the second carrier body 120a) for rotation therewith.

Similarly, the second clutch 64a is configured to selectively non-rotatably couple the second ring gear 116a (rather than the second carrier body 120a) to the housing 40a. In this regard, the second race 236a of the one-way clutch 220a is non-rotatably coupled to the second ring gear 116a, and the third clutch plates 260a of the second friction clutch 222a can be non-rotatably coupled to the second ring gear 116a.

Returning to FIG. 9, the ratchet 452a of the park pawl mechanism 50a can be directly coupled to the first spur gear 314a of the second reduction gearset 68a.

Third Example

Figure 12:
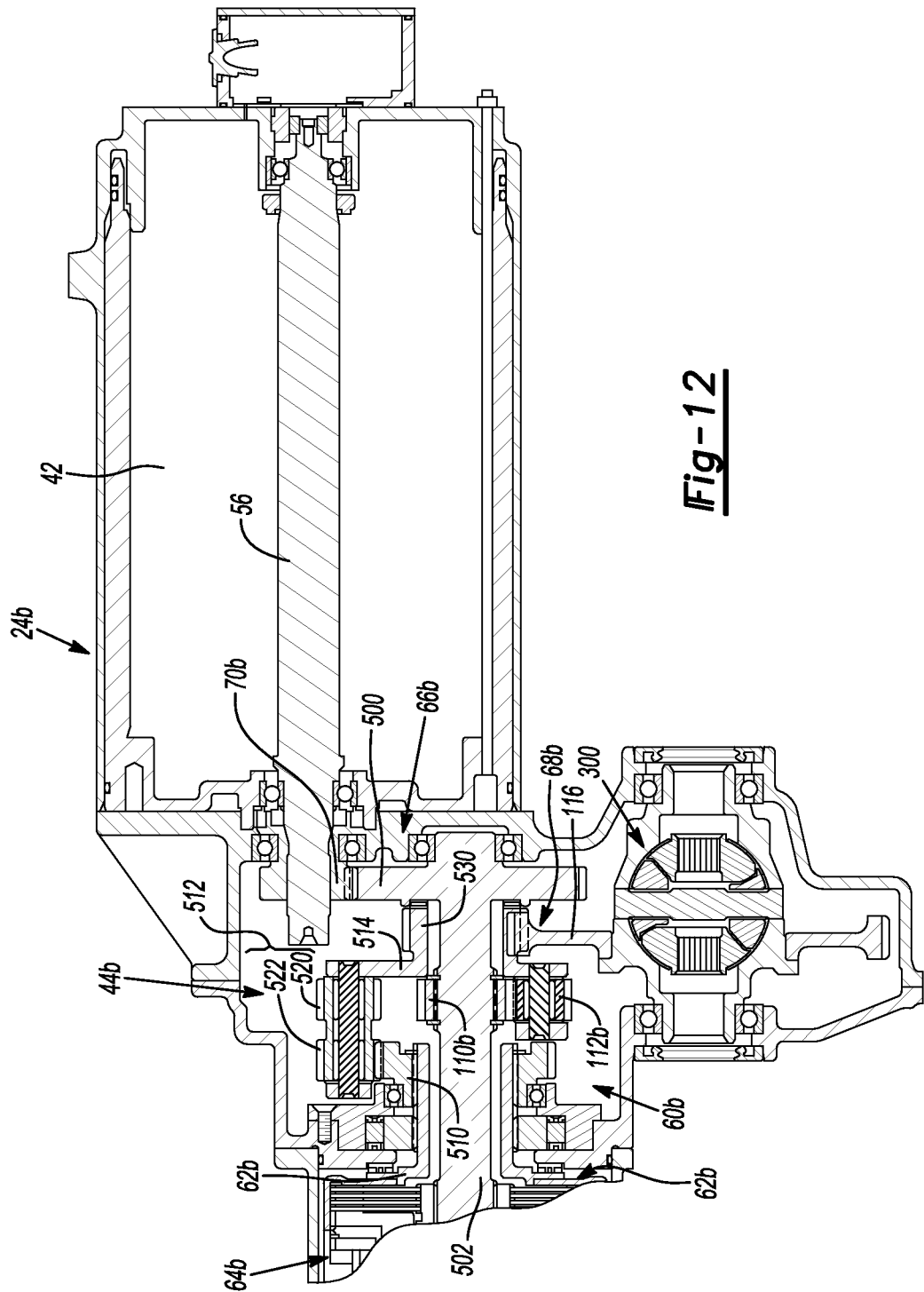
FIG. 12 is a view similar to that of FIG. 2 but depicting another example of a drive module constructed in accordance with the teachings of the present disclosure.

In FIG. 12, a portion of a third drive module 24b constructed in accordance with the teachings of the present disclosure is illustrated. The drive module 24b can be generally similar to the drive module 24 (FIG. 1), except for the construction of the multi-speed transmission 44b.

The multi-speed transmission 44b can comprise a two-speed planetary transmission stage 60b, a first clutch 62b and a second clutch 64b. Optionally, the multi-speed transmission 44b can comprise one or more fixed reduction stages or gearsets, such as a first reduction gearset 66b and a second reduction gearset 68b.

The first reduction gearset 66b can couple the motor output shaft 56 to the two-speed planetary transmission stage 60b. In the example provided, the first reduction gearset 66b comprises a first spur gear 70b that is meshingly engaged to a second spur gear 500 that is coupled to a shaft member 502 for common rotation.

The two-speed planetary transmission stage 60b can include a first sun gear 110b, a second sun gear 510, a plurality of first planet gears 112b, a plurality of compound planet gears 512, and a planet carrier 514. The first sun gear 110b can be coupled to the shaft member 502 for common rotation. The second sun gear 510 can be disposed coaxially about the shaft member 502. Each of the first planet gears 112b can be meshingly engaged with the first sun gear 110b and can be journally supported by the planet carrier 514. Each of the compound planet gears 512 can be journally supported by the planet carrier 514 and can include a second planet gear 520, which can be meshingly engaged to one or more of the first planet gears 112b, and a third planet gear 522 that can be meshingly engaged to the second sun gear 510 and coupled to its associated second planet gear 520 for common rotation. The planet carrier 514 can be the output of the two-speed planetary transmission stage 60b.

The first clutch 62b can be any type of clutch that can selectively couple the second sun gear 510 to the shaft member 502 for common rotation. The second clutch 64b can be any type of clutch or clutches that can be configured to selectively non-rotatably couple the second sun gear 510 to the housing 40b.

The second reduction gearset 68b can include a third spur gear 530, which can be coupled to the planet carrier 514 for rotation therewith, and the second ring gear 116 that can be coupled to the differential case.

The two-speed planetary transmission stage 60b can be operated in a high-speed forward mode in which the first clutch 62b couples the shaft member 502 to the second sun gear 510 and the second clutch 64b does not couple the second sun gear 510 to the housing 40b. Rotary power produced by the motor 42 (through rotation of the output shaft 56 in a first rotational direction) is transmitted through the first reduction gearset 66b to the shaft member 502, which drives both the first sun gear 110b and the second sun gear 510 (through the first clutch 64b). Operation in this manner effectively locks the two-speed planetary transmission stage 60b so that the planet carrier 514 co-rotates with the shaft member 502 to thereby drive the third spur gear 530 at a high speed ratio.

The two-speed planetary transmission stage 60b can also be operated in a low-speed forward mode in which the first clutch 62b does not couple the shaft member 502 to the second sun gear 510 and the second clutch 64 couples the second sun gear 510 to the housing 40b. Rotary power produced by the motor 42 (through rotation of the output shaft 56 in the first rotational direction) is transmitted through the first reduction gearset 66b to the shaft member 502, which drives the first sun gear 110b. The planet carrier 514 is driven by the meshing action of the second planet gears 522 and the second sun gear 510, which drives the third spur gear 530 at a low speed ratio.

The two-speed planetary transmission stage 60b can be operated in a low-speed reverse mode in which the first clutch 62b does not couple the shaft member 502 to the second sun gear 510 and the second clutch 64b couples the second sun gear 510 to the housing 40b.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A drive module comprising:
   an electric motor;
   a differential assembly having a differential input member and a pair of differential output members;
   a multi-speed transmission assembly transmitting rotary power between the electric motor and the differential input member, the multi-speed transmission assembly comprising a housing, a two-speed planetary transmission stage, a first clutch, a second clutch and a transmission output member, the two-speed planetary transmission stage having a sun gear, a ring gear, a plurality of planet gears and a planet carrier, the sun gear being the input of the two-speed planetary stage, the planet gears being meshed with the sun gear and with the ring gear, the planet gears being rotatably mounted on the planet carrier, one of the planet carrier and the ring gear being the output of the two-speed planetary transmission stage and being drivingly coupled to the transmission output member, the first clutch being selectively operable for locking the two-speed planetary transmission stage such that the two-speed planetary transmission stage operates in a 1:1 gear ratio, the second clutch being operable for controlling rotation of the other one of the planet carrier and the ring gear, the transmission output member being meshingly engaged to the differential input member; and a pair of axle shafts, each of the axle shafts being coupled to an associated one of the differential output members for rotation therewith;

wherein the first and second clutches are disposed on a common axial end of the multi-speed transmission assembly.

2. The drive module of claim 1, wherein the multi-speed transmission assembly further comprises a fixed planetary stage.

3. The drive module of claim 2, wherein the fixed planetary stage is disposed between the electric motor and the sun gear of the two-speed planetary transmission stage.

4. The drive module of claim 3, wherein the fixed planetary stage comprises a first planet carrier onto which the sun gear of the two-speed planetary transmission stage is mounted.

5. The drive module of claim 2, wherein the fixed planetary stage is disposed between the two-speed planetary transmission stage and the transmission output member.

6. The drive module of claim 5, wherein the transmission output member is coupled to the ring gear for rotation therewith.

7. The drive module of claim 1, wherein the second clutch comprises a one-way clutch that permits free rotation of the one of the planet carrier and the ring gear in a predetermined rotational direction.

8. A drive module comprising:
an electric motor;
a differential assembly having a differential input member and a pair of differential output members;
a multi-speed transmission assembly transmitting rotary power between the electric motor and the differential input member, the multi-speed transmission assembly comprising a housing, a two-speed planetary transmission stage, a first clutch, a second clutch and a transmission output member, the two-speed planetary transmission stage having a sun gear, a ring gear, a plurality of planet gears and a planet carrier, the sun gear being the input of the two-speed planetary stage, the planet gears being meshed with the sun gear and with the ring gear, the planet gears being rotatably mounted on the planet carrier, one of the planet carrier and the ring gear being the output of the two-speed planetary transmission stage and being drivingly coupled to the transmission output member, the first clutch being selectively operable for locking the two-speed planetary transmission stage such that the two-speed planetary transmission stage operates in a 1:1 gear ratio, the second clutch being operable for controlling rotation of the other one of the planet carrier and the ring gear, the transmission output member being meshingly engaged to the differential input member; and a pair of axle shafts, each of the axle shafts being coupled to an associated one of the differential output members for rotation therewith;

wherein the second clutch comprises a one-way clutch that permits free rotation of the one of the planet carrier and the ring gear in a predetermined rotational direction; and wherein the multi-speed transmission assembly further comprises a third clutch that is selectively operable for inhibiting rotation of the one of the planet carrier and the ring gear in the predetermined rotational direction.

9. The drive module of claim 8, wherein the third clutch is a friction clutch.

10. The drive module of claim 1, wherein the planet gears comprise a set of first planet gears and a set of second planet gears, the first planet gears being meshingly engaged with the sun gear, the second planet gears being meshingly engaged with the first planet gears and the ring gear.

11. The drive module of claim 1, wherein each of the planet gears is meshingly engaged to both the sun gear and to the ring gear.

12. The drive module of claim 7, wherein the multi-speed transmission assembly further comprises a third clutch that is selectively operable for inhibiting rotation of the one of the planet carrier and the ring gear in the predetermined rotational direction.

13. The drive module of claim 12, wherein the third clutch is a friction clutch.

14. A drive module comprising:
an electric motor;
a differential assembly having a differential input member and a pair of differential output members;
a multi-speed transmission assembly transmitting rotary power between the electric motor and the differential input member, the multi-speed transmission assembly comprising a housing, a two-speed planetary transmission stage, a first clutch, a second clutch and a transmission output member, the two-speed planetary transmission stage having a sun gear, a ring gear, a plurality of planet gears and a planet carrier, the sun gear being the input of the two-speed planetary stage, the planet gears being meshed with the sun gear and with the ring gear, the planet gears being rotatably mounted on the planet carrier, the ring gear being the output of the two-speed planetary transmission stage and being drivingly coupled to the transmission output member, the first clutch being selectively operable for locking the two-speed planetary transmission stage such that the two-speed planetary transmission stage operates in a 1:1 gear ratio, the second clutch being operable for controlling rotation of the planet carrier, the transmission output member being meshingly engaged to the differential input member; and a pair of axle shafts, each of the axle shafts being coupled to an associated one of the differential output members for rotation therewith;

wherein the first and second clutches are packaged into a space along a rotational axis of the ring gear such that the first clutch is disposed entirely within the second clutch.

15. The drive module of claim 14, wherein the multi-speed transmission assembly further comprises a fixed planetary stage.

16. The drive module of claim 15, wherein the fixed planetary stage is disposed between the electric motor and the sun gear of the two-speed planetary transmission stage.

17. The drive module of claim 16, wherein the fixed planetary stage comprises a first planet carrier onto which the sun gear of the two-speed planetary transmission stage is mounted.

18. The drive module of claim 14, wherein the second clutch comprises a one-way clutch that permits free rotation of the planet carrier in a predetermined rotational direction.

19. The drive module of claim 18, wherein the multi-speed transmission assembly further comprises a third clutch that is selectively operable for inhibiting rotation of the one of the planet carrier and the ring gear in the predetermined rotational direction.

20. The drive module of claim 19, wherein the third clutch is a friction clutch.

21. The drive module of claim 14, wherein the planet gears comprise a set of first planet gears and a set of second planet gears, the first planet gears being meshingly engaged with the sun gear, the second planet gears being meshingly engaged with the first planet gears and the ring gear.

22. A drive module comprising:
an electric motor;
a differential assembly having a differential input member and a pair of differential output members;
a multi-speed transmission assembly transmitting rotary power between the electric motor and the differential input member, the multi-speed transmission assembly comprising a housing, a two-speed planetary transmission stage, a first clutch, a second clutch and a transmission output member, the two-speed planetary transmission stage having a sun gear, a ring gear, a plurality of planet gears and a planet carrier, the sun gear being the input of the two-speed planetary stage, the planet gears being meshed with the sun gear and with the ring gear, the planet gears being rotatably mounted on the planet carrier, the ring gear being the output of the two-speed planetary transmission stage and being drivingly coupled to the transmission output member, the first clutch being selectively operable for locking the two-speed planetary transmission stage such that the two-speed planetary transmission stage operates in a 1:1 gear ratio, the second clutch being operable for controlling rotation of the planet carrier, the transmission output member being meshingly engaged to the differential input member; and
a pair of axle shafts, each of the axle shafts being coupled to an associated one of the differential output members for rotation therewith;
wherein the housing comprises a wall member that defines an inner annular wall, an intermediate annular wall and an outer annular wall, the intermediate annular wall being received between the inner and outer annular walls, the first clutch comprising a first friction clutch having a first piston, the second clutch comprising a second friction clutch with a second piston, wherein the first piston is disposed radially between the inner and intermediate annular walls, and wherein the second piston is disposed radially between the intermediate and outer annular walls.

* * * * *